United States Patent [19]
Gravlee, Jr.

[11] Patent Number: 5,788,679
[45] Date of Patent: Aug. 4, 1998

[54] PHACOEMULSIFICATION NEEDLE

[76] Inventor: Joseph F. Gravlee, Jr., 557 N. Mobile St., Fairhope, Ala. 36533-1028

[21] Appl. No.: 670,595

[22] Filed: Jun. 26, 1996

[51] Int. Cl.$^6$ .................................................. A61M 5/32
[52] U.S. Cl. .......................... 604/272; 604/22; 606/167
[58] Field of Search ........................ 604/272, 51–53, 604/49, 22, 264; 606/166, 167, 169, 170, 171

[56] References Cited

U.S. PATENT DOCUMENTS

| | | |
|---|---|---|
| 2,555,493 | 6/1951 | Kirschbaum . |
| 3,330,268 | 7/1967 | Goldsmith . |
| 3,589,363 | 6/1971 | Banko et al. . |
| 3,693,613 | 9/1972 | Kelman . |
| 3,805,787 | 4/1974 | Banko . |
| 3,930,505 | 1/1976 | Wallach . |
| 4,027,668 | 6/1977 | Dunn . |
| 4,689,040 | 8/1987 | Thompson . |
| 4,702,260 | 10/1987 | Wang . |
| 4,959,049 | 9/1990 | Smirmaul . |
| 5,162,044 | 11/1992 | Gahn et al. . |
| 5,213,569 | 5/1993 | Davis . |
| 5,254,082 | 10/1993 | Takase . |
| 5,286,256 | 2/1994 | Mackool . |
| 5,292,310 | 3/1994 | Yoon . |

OTHER PUBLICATIONS

Wayne E. Fung, "Phacoemulsification", Clinical Ophthalmology, Chapter 7, vol. 6, pp. 1–16 1993.

*Primary Examiner*—John D. Yasko
*Attorney, Agent, or Firm*—Burns, Doane, Swecker & Mathis, L.L.P.

[57] ABSTRACT

A phacoemulsification needle tip of the present invention has a continuous cutting edge formed at an inner surface of a cylindrical needle shaft. The cutting edge is formed by cutting the needle shaft at an angle and beveling the exterior surface of at least the forward portion of the needle. The beveling of the exterior surface of the needle tip moves the cutting edge from an exterior diameter of the needle to an interior diameter of the needle. The needle tip having the shape of the present invention has improved cutting ability, accuracy, and threading ability which are important for phacoemulsification procedures. The needle tip is also less likely to puncture sensitive membranes of the eye during surgery. The needle tip may also include an internal beveled surface at a trailing portion of the cutting edge.

20 Claims, 5 Drawing Sheets

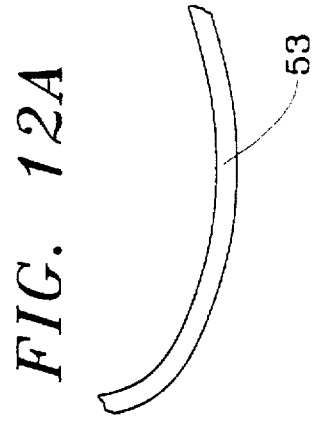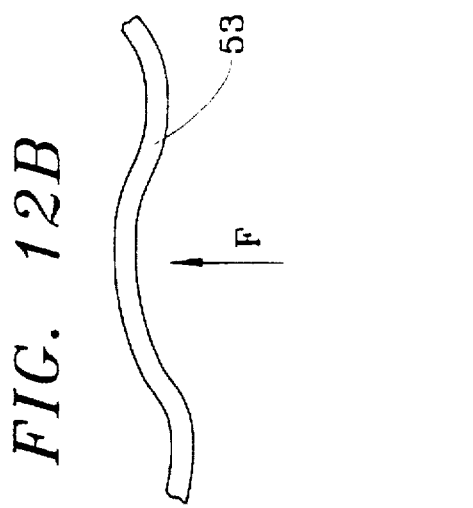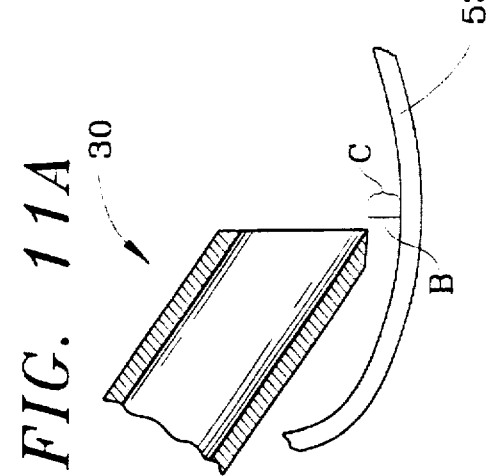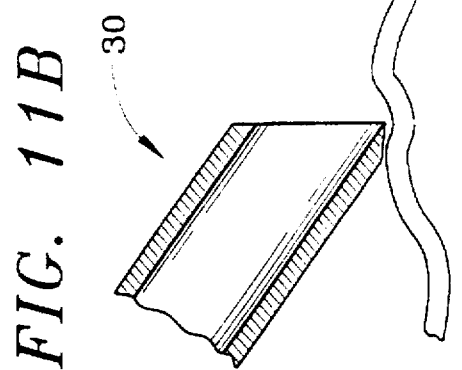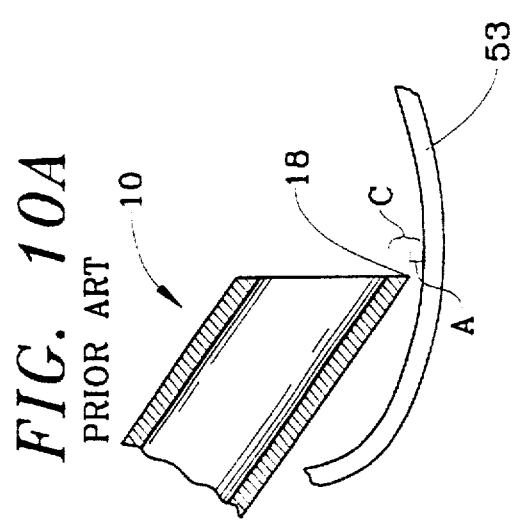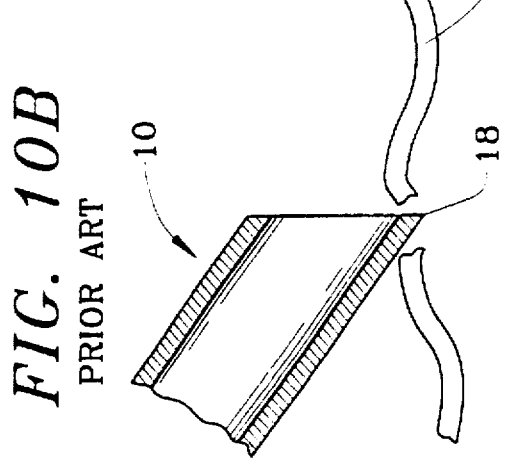

PHACOEMULSIFICATION NEEDLE

FIELD OF THE INVENTION

The present invention relates to a phacoemulsification needle, and more particularly, to a phacoemulsification system and an ultrasonically vibrated phacoemulsification needle tip for breaking apart and removing cataract tissue.

BACKGROUND OF THE INVENTION

Phacoemulsification is a method of removing cataracts through the use of an ultrasonic needle vibrating at ultrasonic frequencies. The vibration of the ultrasonic needle breaks up the cataract into pieces which are emulsified and then gently aspirated out of the eye. This method of cataract removal is preferred in that it requires only a tiny incision at the perimeter of the cornea through which the needle is inserted. Thus, phacoemulsification is considered the least traumatic method of cataract removal. The surgically induced trauma to the eye and the tissues surrounding the eye caused by phacoemulsification surgery is so minimal that it allows the patient to regain vision relatively quickly after the surgery.

A known phacoemulsifier handpiece includes a needle having a needle tip, such as the prior art needle tip 10, shown in FIG. 2, which is vibrated at ultrasonic frequencies to break up the cataract.

The needle tip 10 includes a hollow shaft through which the pieces of a broken up cataract are aspirated from the eye. The shaft of the phacoemulsification needle is generally surrounded by a tubular irrigation sleeve having openings in the side of the sleeve at the distal end and/or at the distal end annulus between the sleeve end and the needle tip, through which irrigation fluid flows to replace the fluid which is aspirated through the needle. The needle and the sleeve together are often referred to as a phacoemulsification probe. The irrigation through the sleeve and aspiration through the needle are carefully controlled to maintain a desired pressure in the chamber of the eye beneath the cornea called the anterior chamber where the cataract is being removed. The pressure in the anterior chamber must be maintained to prevent retinal vascular occlusion due to excessive pressure or collapsing of the anterior chamber due to insufficient pressure.

In operation, the prior art needle tip 10 including the surrounding irrigation sleeve is inserted through a tiny incision at the perimeter of the cornea. A treatment fluid is introduced through the irrigation sleeve. The needle is placed against the lens nucleus containing the cataract and is vibrated at about 40,000 times per second to break up the cataract into microscopic pieces which are suspended in the irrigation fluid "emulsate" and aspirated through the needle.

After the lens content has been completely removed through the needle, leaving the majority of the lens capsule, a specially designed injector, much like a syringe, is often used to implant a foldable intraocular lens in the space where the natural lens has been removed. The injector cartridge is inserted through the tiny corneal incision, and the lens is injected through the center of the pupil where the lens expands and unfolds into position to replace the removed natural lens. Alternatively, a foldable lens can be inserted with special folding forceps, or the incision may be enlarged and a rigid lens may be implanted.

When breaking up and aspirating the lens nucleus it is important to avoid rupturing the posterior capsule of the lens. As the lens nucleus is removed, the posterior capsule effectively becomes a thin diaphragm positioned between the anterior chamber which includes the lens nucleus and the posterior chamber behind the lens nucleus. Rupture of the posterior capsule can be a potentially dangerous complication resulting in secondary vitreous loss and allowing lens particles and other materials to fall into the posterior chamber. If the posterior capsule encounters a sharp instrument such as the prior art needle tip 10, it can be easily broken.

The prior art phacoemulsification needle tip 10, as shown in FIG. 2, includes a cylindrical hollow needle shaft having a needle tip which is cut by a planar surface at an angle of about 60° with respect to the longitudinal axis of the needle. The prior art needle tip 10 has a cutting edge which is shown in FIG. 2A by a bold line 16. As the prior art needle tip 10 is inserted into a mass of tissue such as the lens nucleus, the cutting edge 16 of the needle cuts through the tissue. In particular, the tissue is first cut by the exterior cutting edge 18, shown most clearly in FIG. 2A, which is on the exterior leading edge of the needle 10. As the needle 10 is then advanced into the tissue, the tissue is then cut by the interior cutting edge 20 of the needle. Thus, the exterior cutting edge 18 and the interior cutting edge 20 of the prior art needle 10 are separate disconnected cutting edges which act together to remove tissue. The change of cutting edges from the exterior cutting edge 18 to the interior cutting edge 20 of the needle has a tendency to cause trauma, tearing, resistance or tissue drag, and unnecessary damage to surrounding tissue during cutting. This change of cutting edge is therefore highly undesirable.

The prior art phacoemulsification needle tip 10 has the additional disadvantage that the sharp exterior leading cutting edge 18 of the needle is difficult to thread through tunnel incisions such as the tiny incision in the edge of the cornea. The position of the sharp leading edge of the prior art needle 10 at the exterior surface of the needle increases the tendency for the cutting edge to tear or otherwise damage successive layers of tissue through which the needle is being threaded.

While the cataract is being broken up and emulsified by the vibrating needle, it is not uncommon for the shape of the cataract to change from a generally spherical form to a rather irregular configuration. This is particularly so when the ophthalmologist practices a technique that involves first breaking the cataract into several smaller pieces and then emulsifying the resulting individual pieces. To effectively perform the phacoemulsification procedure, some ophthalmologists prefer that the cataract or piece of cataract be held closely to the tip of the needle (referred to as occlusion of the tip) before application of ultrasonic energy. This can be accomplished most easily when the shape of the cataract or cataract piece has a shape that generally corresponds to the configuration of the needle tip. As shown in FIG. 8, known phacoemulsification needle tips are configured in a way that is not well suited for holding the irregularly configured cataract or cataract piece 80 against the end of the needle by suction because a large gap may be formed between the piece and the suction opening in the end of the needle. As a consequence, since the cataract or cataract piece tends to float around in the anterior chamber, the ophthalmologist must "chase" the cataract or cataract piece around in the anterior chamber in an attempt to effect emulsification. "Chatter" of the cataract or cataract piece occurs due to vibration away from the tip of the needle from the ultrasonic energy when there is incomplete occlusion of the needle tip.

Another disadvantage of the prior art phacoemulsification needle is shown in FIGS. 10A and 10B. FIGS. 10A and 10B illustrate a prior art phacoemulsification needle tip 10. The posterior capsule 53 may be damaged or ruptured by the sharp leading cutting edge 18 of the prior art needle 10, as shown in FIG. 10B. This may occur by pushing the sharp edge of the needle in too far, by aspirating the posterior capsule upward toward the needle, or when the posterior capsule trampolines forward. The posterior capsule 53 may trampoline forward due to a force F caused by vitreous pressure in the posterior chamber or due to vacuum in the anterior chamber. This trampolining of the posterior capsule 53 is illustrated in FIGS. 12A and 12B which show a cross-section of a stretched and a trampolined posterior capsule 53.

SUMMARY OF THE INVENTION

The phacoemulsification needle according to the preferred embodiments of the present invention addresses the disadvantages of the prior art phacoemulsification needles by providing a needle which avoids trauma, tearing, and other unnecessary tissue damage during threading of the needle through tunnel incisions and during cutting of tissue. Further, the present invention provides a needle that is able to readily draw the cataract or cataract pieces to the tip of the needle to thereby facilitate emulsification of the cataract or cataract pieces.

According to one aspect of the invention, a phacoemulsification system for removing cataract tissue from the eye includes an ultrasonic handpiece, a hollow needle mounted on the handpiece, a hollow sleeve surrounding the hollow needle, a treatment fluid delivery system for delivering treatment fluid to the hollow sleeve, and a suction system for aspirating fluid and tissue through the needle. The hollow needle has an internal surface, an external surface, a beveled surface extending substantially around the external surface, and a single continuous cutting edge between the external surface and the internal surface. The cutting edge is formed in a plane which is at an acute angle with respect to an axis of the needle.

According to another aspect of the invention, a phacoemulsification needle includes a hollow needle shaft adapted to be mounted on an ultrasonic handpiece. The hollow needle shaft has an internal surface, an external surface, and a beveled surface extending around a portion of the external circumference of a distal end of the needle shaft. The beveled surface, the external surface and the internal surface form a single continuous cutting edge. The cutting edge has a leading distal edge and a trailing proximal edge.

BRIEF DESCRIPTION OF THE DRAWING FIGURES

The invention will be described in greater detail with reference to the accompanying drawings in which like elements bear like reference numerals, and wherein:

FIGS. 10A and 10B are cross-sectional side views of the prior art needle tip as it comes into contact with the posterior capsule of the lens;

FIGS. 11A and 11B are cross-sectional side views of the needle tip of FIG. 3 as it comes into contact with the posterior capsule of the lens; and FIGS. 12A and 12B illustrate the trampolining of the posterior capsule of the lens due to increased pressure in the posterior chamber or due to decreased pressure in the anterior chamber.

DETAILED DESCRIPTION OF THE PREFERRED EMBODIMENT

Figure 3:
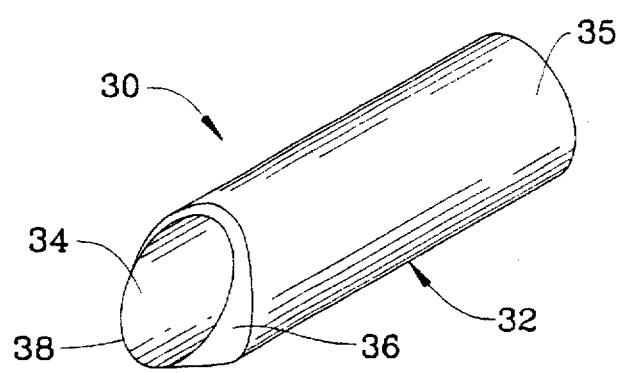
FIG. 3 is a perspective view of a phacoemulsification needle tip according to a first embodiment of the present invention.

A phacoemulsification needle tip 30 according to a first embodiment of the present invention is shown in FIG. 3. The needle tip 30 includes a hollow shaft 32 having a substantially cylindrical inner surface 34 and a substantially cylindrical outer surface 35. The needle has a beveled edge 36 extending between and connecting the inner and outer surfaces of the needle. The beveled edge 36 may be formed by first cutting a continuous cylindrical member at an angle of 15° to 45°, preferably approximately 30°, with respect an axis of the cylinder to form a needle blank having a planar angle cut tip. Thereafter, the outer surface 35 of the distal portion of the angle cut needle blank may be beveled so that a cutting edge 38 of the present invention is formed along the interior surface 34 of the needle tip 30. In this way, the leading cutting edge 38 of the present invention is moved from the prior art position, at the outer diameter or outer surface of the needle shaft, to the inner diameter or inner surface of the needle shaft.

Figure 3A:
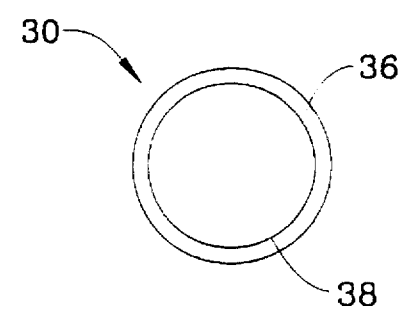
FIG. 3A is an end view of the needle tip of FIG. 3.

As shown in FIG. 3A, the beveling of the edge 36 of the needle 30 according to the first embodiment forms a single continuous cutting edge at the intersection between the beveled edge 36 and the inner surface 34 of the needle shaft 32. This continuous cutting edge possesses a substantially round shape when viewed from the end of the needle shaft as depicted in FIG. 3A. As shown in the cross-sectional view of FIG. 5, the angle α between the beveled edge 36 and the inner surface 34 of the needle shaft at the forward or distal portion of the cutting edge is smaller than the angle β between the beveled edge 36 and the inner surface 34 at the trailing proximal cutting edge. This beveling of the edge provides a sharper leading cutting edge than the prior art needle. This sharper leading cutting edge punctures tissue more easily than the prior art needle. The angle α is between 15° and 45°, preferably about 30°, while the angle β is between 10° and 45°, preferably about 25°.

Figure 5:
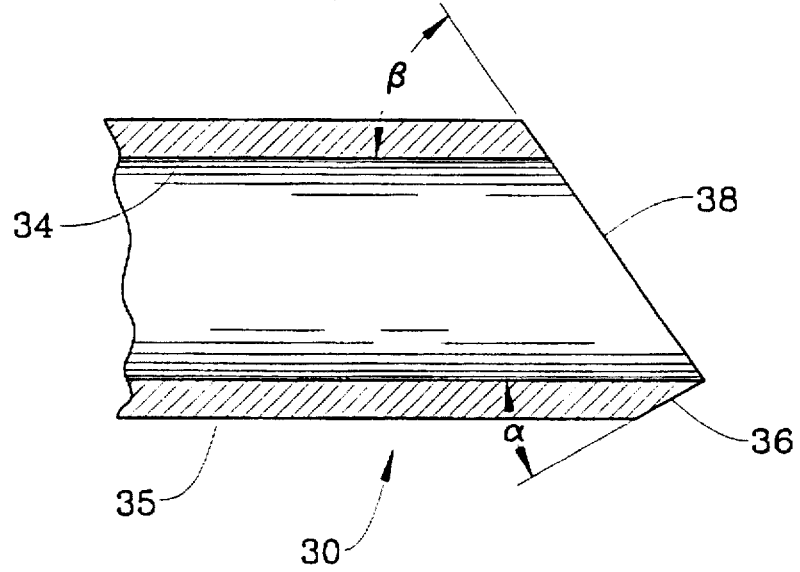
FIG. 5 is a cross-sectional side view of the phacoemulsification needle of FIG. 3.

As shown in FIG. 5, the cutting edge 38 preferably lies entirely within a plane which is at the same angle β as the plane of the beveled edge 36 at the center of the trailing proximal cutting edge. However, the cutting edge 38 may alternatively be formed as a slightly concave or convex edge when viewed from the side of the needle as shown in FIG. 5.

Figure 6:
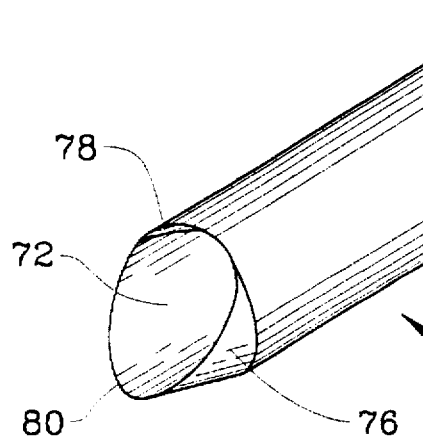
FIG. 6 is a perspective view of a phacoemulsification needle tip according to a second embodiment of the present invention.
Figure 7:
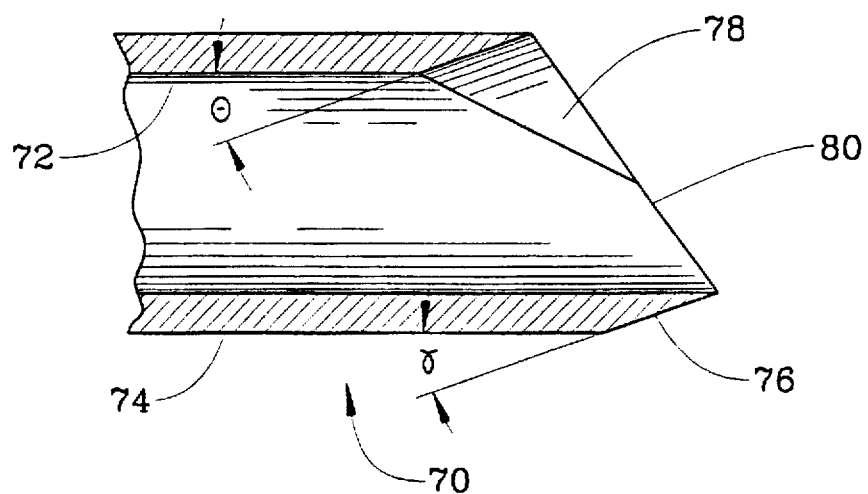
FIG. 7 is a cross-sectional side view of the phacoemulsification needle of FIG. 6.

A phacoemulsification needle tip 70 according to a second embodiment of the present invention is illustrated in FIGS. 6 and 7. The needle tip 70 includes a substantially cylindrical inner surface 72 and a substantially cylindrical outer surface 74. An exterior beveled surface 76 is formed around a portion of the exterior surface of the needle tip and extends about half way around the needle shaft.

Figure 6A:
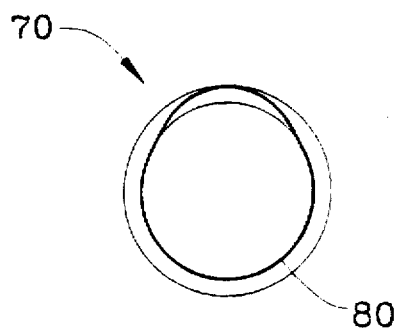
FIG. 6A is an end view of the needle tip of FIG. 6.

In addition, an interior beveled surface 78 is formed around a portion of the inner surface 72 and extends about half way around the interior of the needle shaft. The interior beveled surface 78 is formed at the trailing side of the cutting edge 80. As illustrated in FIG. 6A, the cutting edge 80 is provided at the interior diameter at the leading edge of the needle tip 70 and at the exterior diameter at the trailing edge of the needle tip. As shown in FIG. 7, the exterior beveled surface 76 forms an angle γ with the inner surface of the needle. The interior beveled surface 78 forms an angle θ of between 10° and 45° with the exterior surface 74 of the needle.

The addition of the interior beveled surface 78 provides the advantage of moving the trailing cutting edge 80 away from or radially outwardly from the center of the needle 70 so that the total cutting area of the cutting edge is increased. This increase in the total cutting area is advantageous because it allows more tissue into the needle at one time taking out a larger "core" of tissue and, therefore, may speed up the operation. In addition, the second embodiment of the needle tip 70 provides the same advantages as the first embodiment in that the cutting edge is continuous and thus prevents the tearing which is caused by other known phacoemulsification needles. This embodiment is also advantageous because the needle 70 can be made with a smaller diameter than a prior art needle and work through a smaller wound size, while being just as effective as the larger prior art needle.

Figure 1:
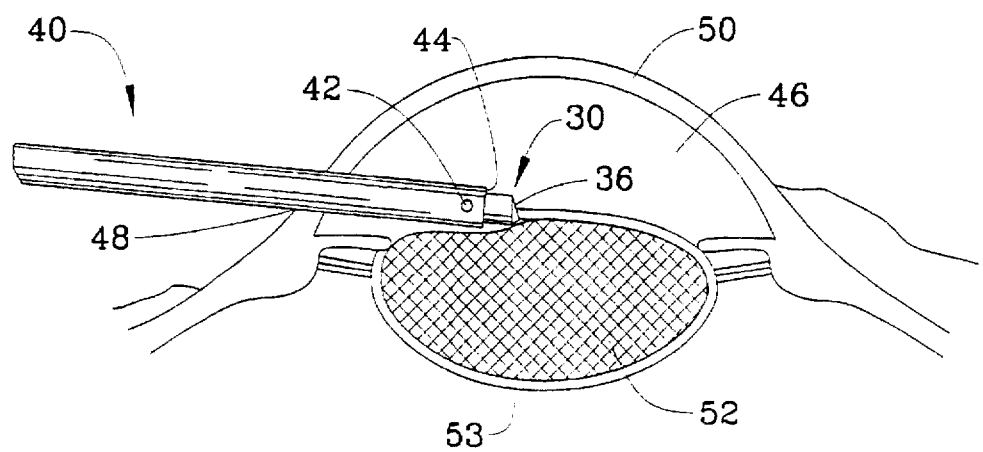
FIG. 1 is a side-sectional view of an eye with a phacoemulsification probe according to the present invention removing a portion of a lens.
Figure 2:
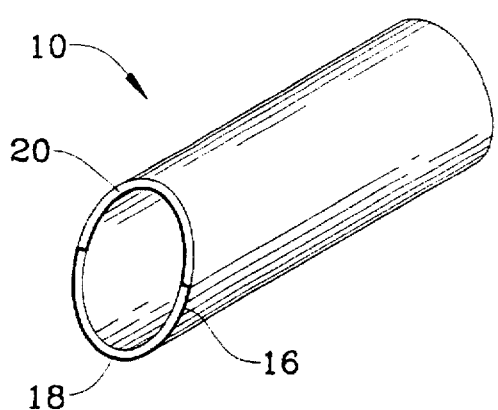
FIG. 2 is a perspective view of a prior art phacoemulsification needle tip.
Figure 2A:
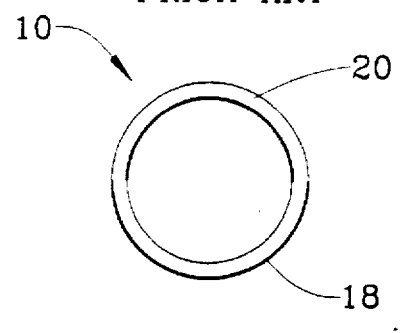
FIG. 2A is an end view of the needle tip of FIG. 2.

As shown in FIG. 1, the needle tip 30 or 70 according to the present invention is surrounded with a hollow irrigation sleeve 40 having an irrigation opening 42 and/or an annular irrigation opening 44 between the end of the sleeve 40 and the exterior of the needle tip 30. As shown in FIG. 1, the needle is inserted into the anterior chamber 46 of the eye through a tiny incision 48 made in the cornea 50. The needle 30 or 70 is then ultrasonically vibrated to break up the lens or cataract 52 into small particles which are emulsified in the irrigation fluid supplied through the sleeve 40 and aspirated through the needle. The entire content of lens 52 is removed using phacoemulsification as well as irrigation and aspiration leaving the membrane as a "capsular bag" and particularly with the posterior capsule 53 intact.

Figure 4:
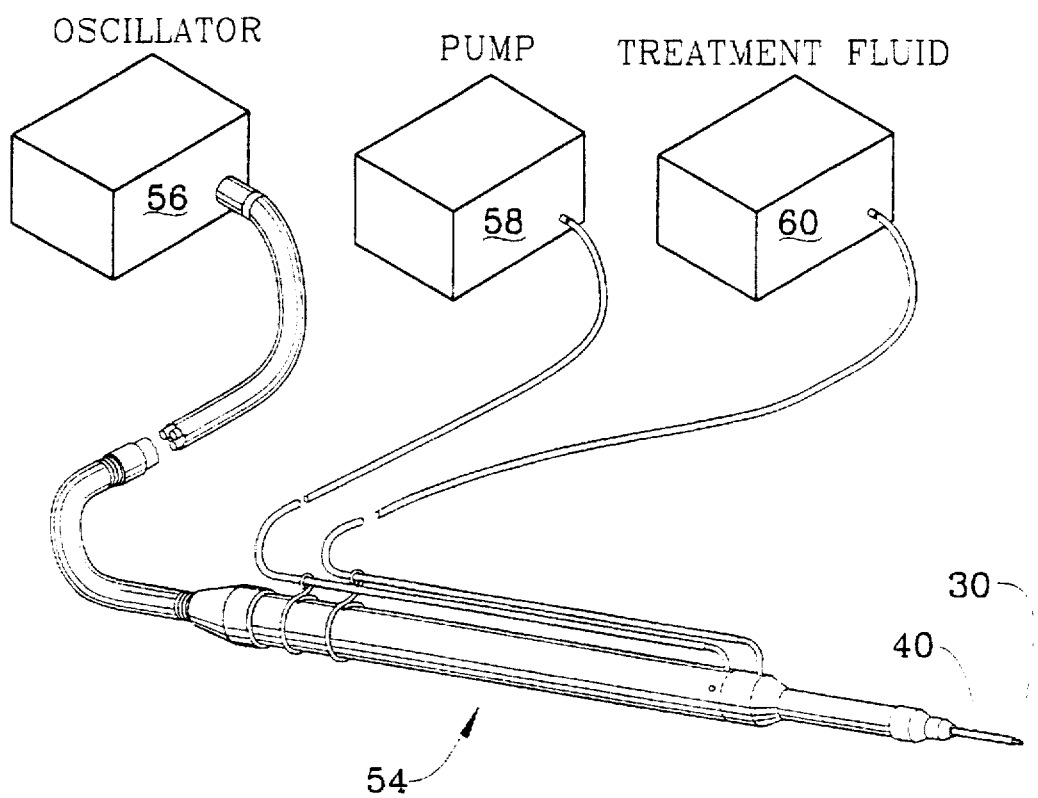
FIG. 4 is a perspective view of a phacoemulsification handpiece system according to the present invention.

A phacoemulsification system employing the needle tip 30 according to the present invention is illustrated in FIG. 4. The system includes a handpiece 54 having the needle 30 attached to a distal end thereof, an oscillator 56, a pump 58, and a treatment fluid supply 60. The needle 30 is surrounded by the irrigation sleeve 40. The oscillator 56 provides ultrasonic vibration of the needle 30 to break up the cataract. The pump 58 provides suction to the interior of the needle and the treatment fluid supply 60 provides treatment fluid to the irrigation sleeve 40. The needle 30 is attached to the handpiece 54 in any known manner, such as, by a threaded connection.

After the lens has been broken up by using the needle 30 or 70 to cut the lens into pieces, many of these pieces will not be small enough to be aspirated through the central lumen of the needle. Large pieces 80 shown in FIGS. 8 and 9 are broken up by using the suction of the probe to capture a piece of lens on the tip of the needle and then ultrasonically vibrating the needle to break the piece captured on the needle into smaller pieces which can be easily aspirated.

Figure 8:
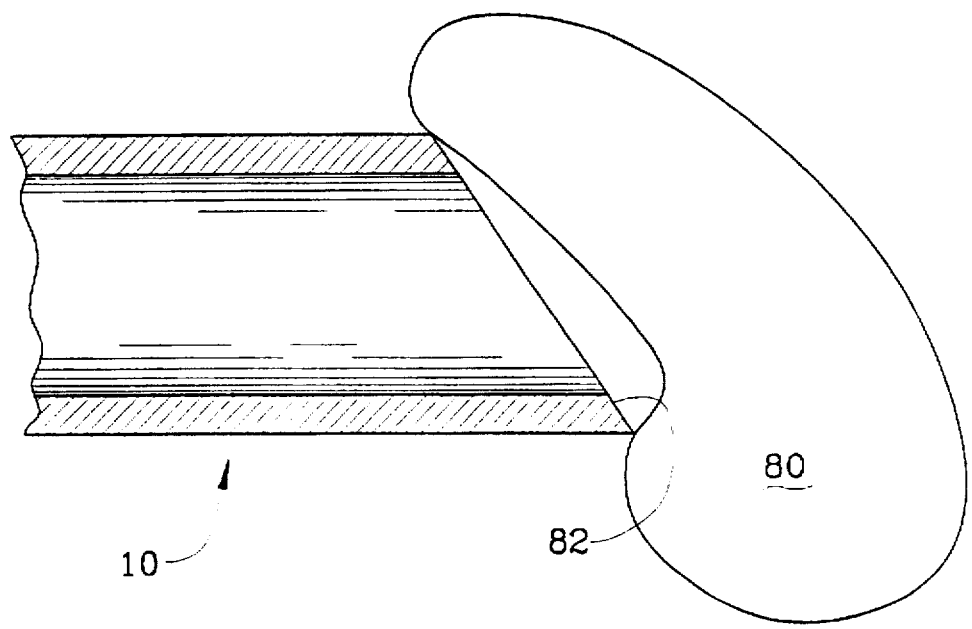
FIG. 8 is a cross-sectional side view of the prior art needle tip as it is used to grasp a piece of tissue.

As shown in FIG. 8, the prior art needle tip 10 has difficulty trapping the large pieces 80 of the lens with the suction because the suction delivery area of the needle tip 10 is surrounded by the planar surface 82 of the cutting tip. This planar surface 82 of the tip may prevent a suction seal from being obtained with the piece to be trapped, particularly, when the piece has an irregular surface.

The advantages of the phacoemulsification needle according to the present invention will be described with respect to the first embodiment of the needle which is shown in FIGS. 3, 3A, and 5. However, these advantages are equally applicable to the second embodiment of the invention which is shown in FIGS. 6, 6A, and 7.

Figure 9:
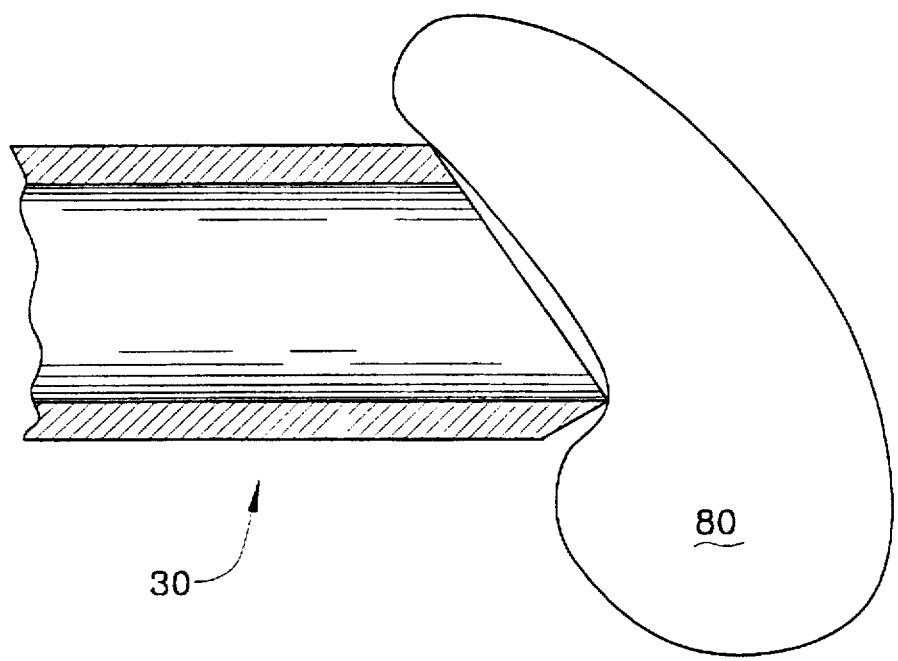
FIG. 9 is a cross sectional side view of the needle tip of FIG. 3 as it is used to grasp a piece of tissue.

As shown in FIG. 9, the present invention allows the lens or pieces of the lens 80 which have broken off to be easily trapped against the needle tip 30 by the force of the suction provided through the central bore of the needle. In the present invention, the needle tip does not have any surfaces surrounding the cutting edge which forms the suction area. Therefore, there are no surfaces which interfere with the creation of a suction between the tip and an irregularly shaped piece 80 of the lens. Therefore, the lens pieces are more easily trapped against the needle 30 and broken into smaller pieces by ultrasonic vibration.

The cutting edge 38 of the present invention which is formed at the inner surface 34 of the needle shaft 32 provides a smaller overall cutting area than a prior art needle of the same size. The smaller cutting area of the present invention is advantageous in some instances because it creates less trauma to tissues surrounding the probe puncture site. The needle tip 30 according to the present invention also has a sharper point than a prior art needle of the same size because the inside diameter of the needle has a smaller arch than the exterior of the needle.

The single continuous cutting edge 38 of the present invention makes a less traumatic cut than the prior art needle which has two distinct cutting edges at the external and the internal surfaces of the needle causing traumatic tearing of the tissue when the cutting operation shifts from one of the cutting edges to the other. The continuous cutting edge 38 punctures the tissue cleanly, whereas, the prior art needle having interior and exterior cutting edges forms a more jagged cut and causes tearing. The continuous cutting edge will be "sharper" because the flat portion will not exist and, therefore, will be a "faster" needle with shorter procedure time.

The nucleus portion of the lens 52 is hard in consistency and is difficult to cut. However, the needle tip 30 according to the present invention cuts through the nucleus portion of the lens more easily than the prior art needle because it has a sharper cutting edge than the prior art needle, it has a smaller cutting area than the prior art needle, and the continuous cutting edge slices through tissue more easily with less resistance than the discontinuous cutting edge of the prior art needle.

The needle tip 30 according to the present invention is also easier to thread through a tunnel incision, such as, the tiny corneal incision 48, corneal-sclera tunnel incisions, or sclera incisions than the prior art needle tip 10. In particular, the leading external cutting edge 18 of the prior art needle tends to catch on the tissue within the tunnel incision and damage the tissue. In contrast, the needle tip 30 according to the present invention having the cutting edge 38 positioned toward the center of the needle does not catch as easily on the walls of the tunnel incision during threading because the beveled surface 36 and the outer surface 35 of the needle help to push the tissue away from the cutting edge 38 of the needle during threading.

Puncturing of the posterior capsule 53 of the lens is a common surgical complication which leads to the serious complication of vitreous loss. The posterior capsule 53 is more likely to rupture if it trampolines forward, as shown in FIG. 12B, due to vitreous pressure of fluid gradients and contacts the sharp leading tip of the prior art needle 10 than if it contacts the needle tip of the present invention. With the present invention there is less chance of posterior capsule rupture because the edge of the needle 30 presented to the posterior capsule 53 is relatively blunt. In addition, when the leading edge of the internal bore of the needle 10 of the prior art (FIG. 10A) and the needle 30 according to the invention (FIG. 11A) are located the same distance C from the posterior capsule 53, the posterior capsule travels a distance A to touch the needle 10 of the prior art and a distance B to touch the needle 30 of the present invention. The distance A is smaller than the distance B, thus the less movement of the posterior capsule will cause rupture in the prior art.

The needle according to the present invention may also provide a better delivery pattern of phacoemulsification energy to the tissue to be removed because the energy will be more focused, as opposed to the prior art needles in which the shock waves emanating from the flat surfaces of the prior art needle are more generalized. This better energy distribution will likely create less cavitation bubbles which obstruct the surgeon's view of the operating site. Also, this better energy distribution will likely cause less traumatic damage to the corneal endothelial cells and less overall energy utilization.

While the invention has been described in detail with reference to preferred embodiments thereof, it will be apparent to one skilled in the art that various changes can be made, and equivalents employed without departing from the spirit and scope of the invention.

What is claimed is:

1. A phacoemulsification system for removing cataract tissue from the eye comprising:
an ultrasonic handpiece;
a hollow needle mounted on the handpiece, the hollow needle having an internal surface, an external surface, an angled tip a beveled surface extending substantially around the external surface at the angled tip, and a single continuous cutting edge between the external surface and the internal surface, the cutting edge extending substantially all the way around the hollow needle and having a leading portion of the cutting edge formed along an inner diameter of the hollow needle;
a hollow sleeve surrounding the hollow needle;
a treatment fluid delivery system for delivering treatment fluid to the hollow sleeve; and
a suction system for aspirating fluid and tissue through the hollow needle.

2. The phacoemulsification system according to claim 1, wherein the beveled surface extends around the entire circumference of the needle tip and the cutting edge is formed at the intersection of the beveled surface and the internal surface.

3. The phacoemulsification system according to claim 2, wherein the beveled surface of the needle forms a first angle with the internal surface of the needle along a first annular portion of the needle, and the beveled surface forms a second angle with the internal surface along a second annular portion of the needle, wherein the first angle is greater than the second angle.

4. The phacoemulsification system according to claim 3, wherein the first side is a side of the needle having a leading portion of the cutting edge and the second side is a side of the needle having a trailing portion of the cutting edge.

5. The phacoemulsification system according to claim 1, wherein the beveled surface has a planar cross-section.

6. The phacoemulsification system according to claim 1, wherein the internal surface of the hollow needle has an internal beveled surface.

7. The phacoemulsification system according to claim 6, wherein the cutting edge includes a leading portion formed at the intersection between the beveled surface and the internal surface, and a trailing portion formed at the intersection between the internal beveled surface and the external surface.

8. The phacoemulsification system according to claim 6, wherein the beveled surface and the internal beveled surface each extend around approximately half of a circumference of the needle tip on opposite sides of the needle tip.

9. The phacoemulsification system according to claim 1, wherein the entire cutting edge lies in a plane which is at an acute angle with respect to the longitudinal axis of the hollow needle shaft.

10. The phacoemulsification system according to claim 1, wherein the single continuous cutting edge is formed at the internal diameter of the hollow needle.

11. The phacoemulsification system according to claim 1, wherein the single continuous cutting edge is formed at the internal diameter of the hollow needle at a leading edge of the cutting edge and at an external diameter of the hollow needle at a trailing edge of the cutting edge.

12. A phacoemulsification needle comprising:
A hollow needle shaft adapted to be mounted on an ultrasonic handpiece, the hollow needle shaft having an internal surface, an external surface, an angled distal end, and a beveled surface extending around a portion of the external circumference of the distal end of the needle shaft, a single continuous, substantially oval-shaped cutting edge formed by intersections of the beveled surface, the internal surface, and the external surface, the cutting edge having a leading distal edge and a trailing proximal edge.

13. The phacoemulsification needle according to claim 12, wherein the entire cutting edge lies in a plane which is at an acute angle with respect to an axis of the hollow needle shaft.

14. The phacoemulsification needle according to claim 12, wherein the beveled surface extends around the entire external circumference of the distal end of the needle shaft and forms a first angle with the internal surface at the leading distal edge and a second angle with the internal surface at the trailing proximal edge, wherein the first angle is greater than the second angle.

15. The phacoemulsification needle according to claim 13, wherein the angle of the plane with respect to the axis of the needle shaft is the same as an angle between the beveled surface and the internal surface at the trailing proximal edge.

16. The phacoemulsification needle according to claim 12, wherein the beveled edge has a planar cross-section.

17. The phacoemulsification needle according to claim 12, wherein the cutting edge forms an oval shape.

18. The phacoemulsification needle according to claim 12, wherein the internal surface includes an internal beveled surface.

19. The phacoemulsification needle according to claim 18, wherein the cutting edge includes a leading portion formed at the intersection between the beveled surface and the internal surface, and a trailing portion formed at the intersection between the internal beveled surface and the external surface.

20. The phacoemulsification needle according to claim 18, wherein the beveled surface and the internal beveled surface each extend around approximately half of the circumference of the needle shaft on opposite sides of the needle tip.

* * * * *